United States Patent
Miller

(12) 
(10) Patent No.: US 11,732,910 B2
(45) Date of Patent: Aug. 22, 2023

(54) HUMIDIFIER ARRANGEMENTS AND CONTROL SYSTEMS

(71) Applicant: Fisher & Paykel Healthcare Limited, Auckland (NZ)

(72) Inventor: Jeremy Livingston Miller, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/445,485

(22) Filed: Aug. 19, 2021

(65) Prior Publication Data

US 2022/0099315 A1    Mar. 31, 2022

Related U.S. Application Data

(60) Continuation of application No. 16/740,837, filed on Jan. 13, 2020, now Pat. No. 11,125,451, which is a continuation of application No. 16/033,072, filed on Jul. 11, 2018, now Pat. No. 10,578,324, which is a continuation of application No. 15/659,380, filed on Jul. 25, 2017, now Pat. No. 10,047,964, which is a division of application No. 14/528,887, filed on Oct. 30, 2014, now Pat. No. 9,726,390.

(60) Provisional application No. 61/897,471, filed on Oct. 30, 2013.

(51) Int. Cl.
| | |
|---|---|
| *F24F 6/02* | (2006.01) |
| *A61M 16/16* | (2006.01) |
| *A61M 16/00* | (2006.01) |
| *F24F 6/00* | (2006.01) |
| *F24F 140/30* | (2018.01) |

(52) U.S. Cl.
CPC .......... *F24F 6/025* (2013.01); *A61M 16/024* (2017.08); *A61M 16/16* (2013.01); *A61M 2205/15* (2013.01); *A61M 2205/3317* (2013.01); *F24F 2006/008* (2013.01); *F24F 2140/30* (2018.01)

(58) Field of Classification Search
CPC ............... A61M 16/024; A61M 16/16; A61M 2205/15; A61M 2205/3317; F24F 6/025; F24F 2006/008; F24F 2140/30
USPC ................................ 261/128, 131, 135, 142
See application file for complete search history.

(56) References Cited

U.S. PATENT DOCUMENTS

| | | |
|---|---|---|
| 5,339,383 A | 8/1994 | Marino |
| 6,175,310 B1 * | 1/2001 | Gott ..................... G01M 3/165 73/40 |
| 7,109,444 B2 | 9/2006 | Levy et al. |
| 7,942,389 B2 | 5/2011 | Koch et al. |
| 8,511,651 B2 | 8/2013 | Fridberg et al. |
| 9,726,390 B2 | 8/2017 | Miller |
| 9,821,135 B2 | 11/2017 | Tang et al. |
| 10,047,964 B2 | 8/2018 | Miller |
| 10,317,098 B2 | 6/2019 | Bayer et al. |
| 10,578,324 B2 | 3/2020 | Miller |

(Continued)

FOREIGN PATENT DOCUMENTS

WO    WO 2012/171072    12/2012

*Primary Examiner* — Charles S Bushey
(74) *Attorney, Agent, or Firm* — Knobbe, Martens, Olson & Bear, LLP

(57) ABSTRACT

The electrical connections of a chamber or enclosure for a water tub can be protected through the use of spill element sensors. The spill element sensors can help to disable the delivery of power to the heater of a water tub in the event that the electrical connections become wet.

20 Claims, 6 Drawing Sheets

(56) References Cited

U.S. PATENT DOCUMENTS

| | | |
|---|---|---|
| 11,125,451 B2 | 9/2021 | Miller |
| 2009/0283923 A1 | 11/2009 | King |
| 2011/0163170 A1 | 7/2011 | Feldstein et al. |
| 2014/0202460 A1 | 7/2014 | Bath et al. |
| 2022/0008681 A1* | 1/2022 | Ghalib .................. A61M 16/16 |
| 2022/0072261 A1* | 3/2022 | Virr ..................... A61M 16/142 |
| 2022/0218936 A1* | 7/2022 | Potharaju .......... A61M 16/1075 |
| 2022/0218938 A1* | 7/2022 | Virr ................... A61M 16/1095 |

* cited by examiner

HUMIDIFIER ARRANGEMENTS AND CONTROL SYSTEMS

CROSS-REFERENCE TO RELATED APPLICATIONS

This application is a continuation of U.S. patent application Ser. No. 16/740,837, filed Jan. 13, 2020, entitled "HUMIDIFIER ARRANGEMENTS AND CONTROL SYSTEMS", now U.S. Pat. No. 11,125,451, which is a continuation of U.S. patent application Ser. No. 16/033,072, filed Jul. 11, 2018, entitled "HUMIDIFIER ARRANGEMENTS AND CONTROL SYSTEMS", now U.S. Pat. No. 10,578,324, which is a continuation of U.S. patent application Ser. No. 15/659,380, filed Jul. 25, 2017, now U.S. Pat. No. 10,047,964, entitled "HUMIDIFIER ARRANGEMENTS AND CONTROL SYSTEMS", which is a divisional of U.S. patent application Ser. No. 14/528,887, filed Oct. 30, 2014, entitled "HUMIDIFIER ARRANGEMENTS AND CONTROL SYSTEMS", now U.S. Pat. No. 9,726,390, which claims priority to U.S. Provisional Application No. 61/897,471, filed Oct. 30, 2013, entitled "HUMIDIFIER ARRANGEMENTS AND CONTROL SYSTEMS", which is incorporated by reference herein in its entirety. Any and all applications for which a foreign or domestic priority claim is identified above or in the Application Data Sheet as filed with the present application are hereby incorporated by reference under 37 CFR 1.57.

BACKGROUND

Field

The present disclosure generally relates to devices for humidifying respiratory gases. More particularly, the present disclosure relates to heating arrangements, sensors, and control systems for use with devices for humidifying respiratory gases.

Description of Related Art

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other disorder. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression, and anxiety.

In general, respiratory disorders are commonly treated by the application of gases at a pressure or flow greater than normally experienced by the patient under ambient conditions. In order to ameliorate discomfort and/or mucosal tissue damage that may rise from administration of cold and/or dry gases, the gas used to treat the respiratory disorder may be humidified. In some configurations, the gas may be humidified by forcing the gas to travel through a passover-type humidification chamber containing water and a heater for heating said water. In such a configuration, the heater encourages the evaporation of the water, which in turn imbues the stream of air with moisture.

SUMMARY

In many humidification systems for humidifying respiratory gases, water is placed into a tub (or a chamber) by a user and in some cases the tub is removed before the tub can be filled. In some cases, the humidification system may be moved when water is in the tub. In such cases, there is an increased risk that the user may spill water into the chamber or housing of the system when handling the tub or filling the tub. If the water is spilled onto, for example, the electrical connections for a heating device (e.g., a heater plate) that sits within the chamber, it is possible that the exposure to water may corrode the connections. Additionally, the spillage of large quantities of water within the enclosure can lead to undesirable situations. In some configurations, a base unit can include electrical contacts configured to provide electrical power to a heater plate integrated into a water tub. Water spillage onto the base unit may cause electrical shorts and/or other undesirable situations. Thus, it is an object of the disclosure to provide an improved humidification system that might solve one or more of the above problems, or at least provide the public with a useful choice.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION

An aspect of at least one of the configurations disclosed herein includes the realization that exposed electrical connections in a humidification system may be protected through the use of water sensing elements that can be used to help to limit or disconnect the supply of power to such electrical connections.

Figure 1:
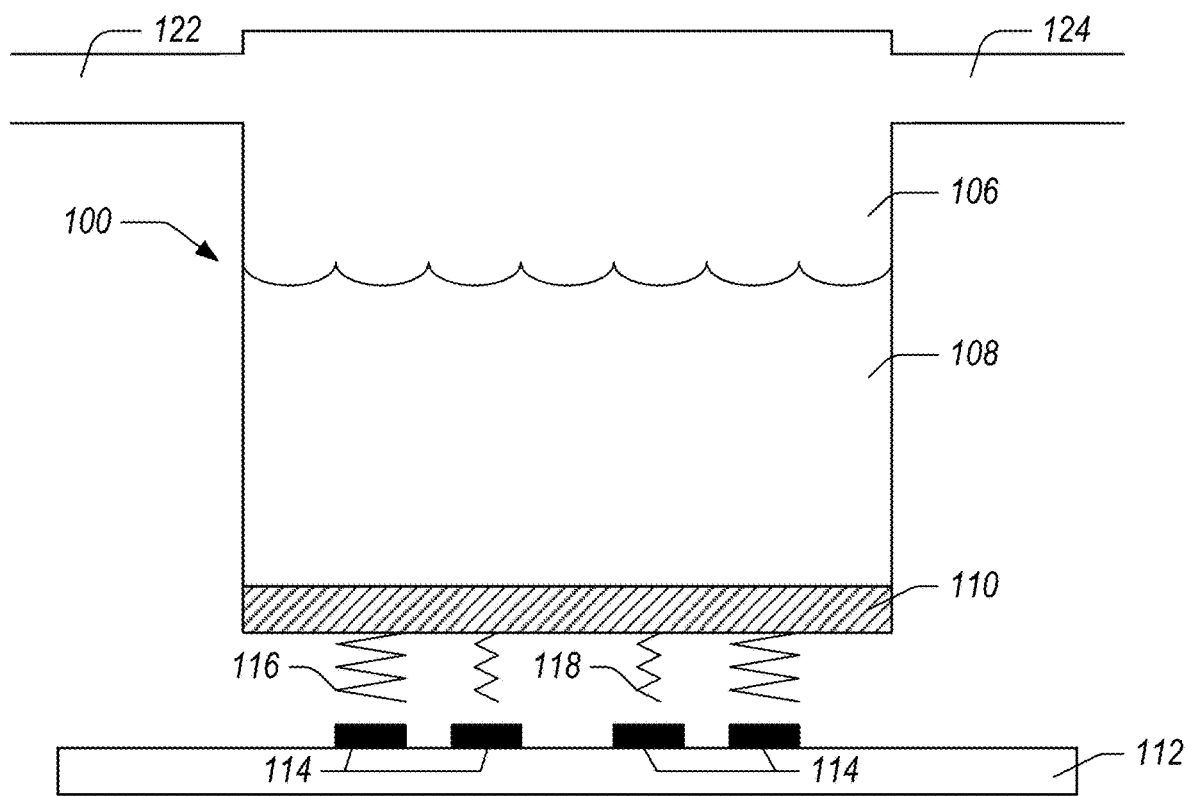
FIG. 1 is a depiction of a humidification system.

With reference to FIG. 1, a humidification system 100 for use with a respiratory therapy device is shown. The system 100 shown may comprise a tub 106. The tub 106 may in use store a quantity of water 108 or other humidification agent. A base unit, chamber, humidification compartment, or enclosure 112 may support the tub 106. The tub 106 may comprise a gas inlet 122, a gas outlet 124, and a heating element 110 that may be used to heat the water 108 in the tub 106 so that gases moving through the tub 106 from the inlet 122 in use may be heated and moistened with water vapour before moving through the outlet 124. The tub 106 may also comprise an aperture (not shown) that may be used to fill the tub 106 with water 108. Conduits (not shown) may be used to carry gas from a gas source (not shown) to the tub 106, and from the tub 106 to a patient or patient interface (not shown). The heating element 110 may be any means, structure or configuration by which heat may be generated and supplied to heat the water 108 in the tub 106.

In some configurations, the tub 106 may be formed from a plastic resin. In some configurations, the heating element 110 may be a metallic resistive heater plate that may heat the water 108 in the tub 106. In some configurations, the heating element 110 may comprise a resistive foil/film/ink that has been cut, stamped, printed, and/or etched to form a particular shape or area that is effective for promoting heating in the water 108. In some configurations, the heating may be even heating. In some configurations, the heating element 110 may comprise a resistive wire embedded within or on a substrate. In some configurations, the heating element 110 may comprise a resistive material that has been etched or printed onto material that may reside on a substrate. In some configurations, the heating element 110 may be on or in a surface of, or integrally formed with, the tub 106. In some configurations, the heating element 110 may be on or in a surface of, or integrally formed with, the base unit 112.

Figure 2:
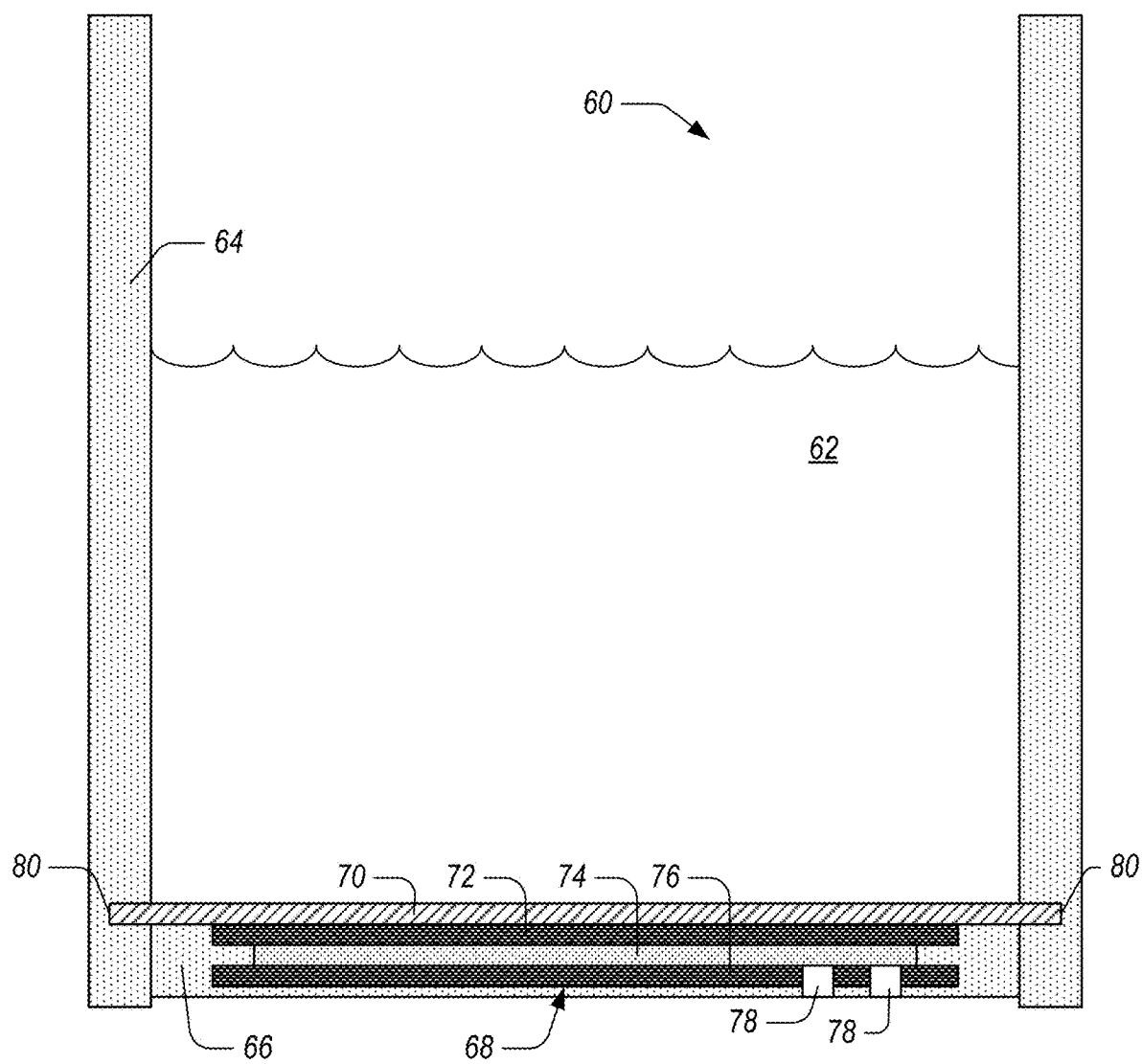
FIG. 2 illustrates an example water tub with an integrated heater element.

FIG. 2 illustrates an example embodiment of a water tub 60 with an integrated heater element 68. The heater element 68 may be a metallic printed circuit board (PCB) and may comprise tracks of conductive metallic foils arranged on the PCB. In an example, the heating element may include conductive metallic foils, e.g., a copper foil, arranged in a serpentine pattern on the dielectric laminate layer. The heating element may have a direct current (DC) resistance in a range of about 5 to 25 Ohms, e.g., 5-15 Ohms, at room temperature. The thickness of each track of the heating element may be in a range, for example, of about 0.4 mm to 1 mm. In some implementations, the tub 60 can include the heating element that includes a PCB-type substrate. The substrate may include a metallic layer, a copper layer, and a dielectric laminate layer between the metallic layer and the copper layer. The metallic layer may be constructed of aluminum, stainless steel, other heat conductive metals, or even other types of PCB substrates. The dielectric laminate layer may be constructed of a ceramic or polymeric material. The heating tracks may be etched in the copper or heating alloy layer. A protective layer may be printed onto at least the copper layer.

To supply power to the heating element 110 and thereby generate heat, an electrical connection between the heating element 110 and the base unit 112 may be used. Any means, structure or configuration for establishing an electrical connection between the heating element 110 and the base unit 112 may be used. In some configurations, the heating element 110 may comprise spring contacts 116, 118 that can contact conductive pads or terminals 114 on the base unit 112. In some configurations, the heating element 110 may comprise conductive pads or terminals 114 that can contact spring contacts 116, 118 on the base unit 112. In some configurations, the element 110/unit 112 connection may be a loose drop-in style connection. In some configurations, the element 110/unit 112 connection may be a tongue-and-groove style connection similar to that found in a typical wall socket. The element 110 may comprise one or more tongues (not shown) that may fit into one or more corresponding grooves (not shown) on the unit 112. Alternatively, or in addition to the above, the unit 112 may comprise one or more tongues that may fit into one or more corresponding grooves on the element 110. In some configurations, the contacts 116, 118 can be electrically conducting pads configured to contact spring-loaded terminals on the base unit 112. The electrically conducting pads can protrude from the bottom of the tub 106. In some configurations, the contacts 116, 118 can be spring-loaded plungers configured to contact corresponding conductive receptors that can be flat, protruding, or recessed relative to a surface on the base unit 112. In some embodiments, the contacts 116, 118 and terminals 114 can be mechanically configured to allow the tub to be seated onto the base unit 112 so that rotation of the tub 112, when seated, is resisted due to the mechanical contact of the contacts 116, 118 and terminals 114. This can advantageously ensure electrical contact in the presence of movement or disturbance of the humidification system 100.

The electrical terminals may connect the heating element 110 to a controller that may be connectable to a power source, such as an electrical wall socket. The controller may regulate the voltage or current applied to the heating element 110. In an example, the controller may provide one or more of the following: power switch, temperature sensing, fault detection (e.g., open, short, over temperature, poor connection, sensor, water ingress to PCB, CPU, power device, power switch), fault protection, and/or electrical interfacing to the heating element 110.

FIG. 2 shows a humidifier tub or water tub 60 for heating water 62 according to embodiments described herein. The tub 60 includes sidewalls 64, or sidewall portions, or tub sidewalls extending around the entire perimeter of the tub and a bottom wall 66 which joins to the sidewalls. A heating apparatus or heating assembly 68 is incorporated into the bottom wall 66. In an example, the sidewalls 64 and bottom wall 66 (e.g., formed of plastic) are overmolded onto the heating apparatus 68. In the illustrated example, the bottom wall 66 is molded over peripheral edges of the dielectric layer 72, heating element 74, and protective layer 76. In some implementations, the protective layer may cover one or more layers of the heating apparatus.

The heating apparatus 68 is formed as a lamination of a hot plate 70, a thermally conductive dielectric layer 72, a heating element 74 and a protective layer 76. The hot plate may be a metal plate having a first side with an anodized coating which is adapted to form the bottom interior surface of the tub exposed to the water 62. The opposite side of the hot plate receives the thermally conductive dielectric layer 72 which may be a resin with dielectric particles.

The heating element 74 may be a serpentine track of a metallic foil, e.g. forming a serpentine track of conductive foil, that is printed on or otherwise applied to a side of the dielectric layer 72 opposite to the hot plate 70. Contact pads 78 may be arranged at each of the ends of the track of the heating element or close to the edge of the hot plate to allow for a spring electrical contact. The contact pads 78 may be exposed through the protective layer 76. Further the contact pads may be formed with raised terminals which protrude slightly from the bottom wall 66 of the tub. Such arrangement allows the contact pads 78 to engage power terminals at, for example, the bottom of a humidifier chamber which provides electrical power to the heating element. In use, the exposed contact pad 78 may engage a power terminal or spring electrical contact at the bottom of a humidifier chamber when the tub is engaged with the humidifier chamber, e.g., a push-down or drop-in electrical contact connection configuration.

As described herein, the heating apparatus 68 may have exposed contact points (e.g., exposed contact pads 78) so that when the tub is placed on the bottom of the humidifier chamber, the contact points engage with counterpart contact points adapted to supply electrical power. In such example, the contact points within the humidifier chamber may be spring loaded, so that such contact points must be depressed to effect an electrical connection, e.g., contact points within the humidifier chamber engage only when the humidifier lid is closed to retain the humidifier tub within the humidifier chamber.

The heating element 74 may be formed of electrical resistance heating materials such as copper, electrical heating alloys such as Iron-Nickel, Copper-Nickel, Iron-Chromium-Aluminum, Nickel-Chromium, as well as other materials such as PTC ink materials, Carbon ink materials, copper foil, and other materials having a relatively low electrical resistance or combinations thereof. The heating element 74 may comprises metallic foils, tracks or strips arranged in a serpentine pattern, such as in rows. The heating element 74 may be printed or applied to the dielectric layer 72. The layout of the heating element and the shape of the serpentine pattern may depend on the shape of the bottom plate 66 of the tub. In use, the heating element 74 converts electrical power to heat energy. The heating element 74 can be configured in a track layout or pattern. The tracks or strips can be arranged in a concentric ring-like manner. Advantages of this layout include improved thermal distribution as well as improved tolerance for thermal expansion/contraction of the tracks as it heats/cools. This layout may also improve the resistance accuracy during the heating process.

The protective layer 76 may comprise materials commonly used for "solder masks," for example polymer or acrylic. Solder masks are conventionally printed on or otherwise applied to coat a printed circuit board (PCB), thermally conductive laminate layer and conductive traces of the heating element during PCB and metal core printed circuit board (MCPCB) manufacturing processes. In the context of the heating apparatus, the protective layer 76 may be printed on or otherwise applied to coat the heating element 74 and the dielectric layer 72. The heating element 74 can be sandwiched between the protective layer 76 and the dielectric layer 72. The protective layer 76 may extend over the peripheral edges of the heating element 74 and directly coat portions of the dielectric layer 72. Exemplary materials for the protective layer 76 include, for example, screen printable epoxy mask, liquid photoimageable solder mask (IPSM) and dry film photoimageable solder mask (DFSM). Contact pads and/or other conductive portions of the heating element may be exposed through the protective layer 76 to allow for connection of the electrical leads to the heating element, e.g., by surface mounting technology.

The dielectric layer 72 may be a coating, layer or board bonded to the hot plate. The dielectric layer 72 comprises materials which have good thermal conductivity properties, but are low in electrical conductance, e.g., relatively high electrical resistance, and thus may be referred to as a dielectric laminate layer. The dielectric layer 72 may be a composite layer of dielectric particles embedded in a filler material, such as a resin. For example, the dielectric layer 72 may include electrically insulating dielectric materials, such as ceramics, polymers, polymer and ceramic, polymer mixed with inorganic particles, ceramics coated with polytetrafluoroethylene, e.g., Teflon®, polyimides, boron nitride, alumina, beryllium oxide, aluminum nitride, boron nitride, epoxy composite, and reinforced fiberglass, arranged to form an electrical insulating layer. In an example, the dielectric breakdown voltage of the laminate layer may be above 2 kV. Further, the dielectric layer 72 may be rigid or flexible, and may be planar or have some other shape which may conform to a bottom and/or side of the tub.

During use of the humidification system 100, it is possible that the user may, for example when filling the tub 106, spill some water into the recess between the tub 106 and the base unit 112, causing water to collect on the springs 116, 118 or the terminals 114. A spill may also occur if the humidification system 100 or a respiratory therapy system or enclosure comprising the humidification system 100 is moved and/or transported with a partially or fully filled tub/chamber. Moisture on the electrical connections of the system 100 may cause the springs 116, 118 and/or the terminals 114 to corrode electrolytically and/or over a period of time, decreasing the efficacy or usability of the heating element 110.

Figure 3:
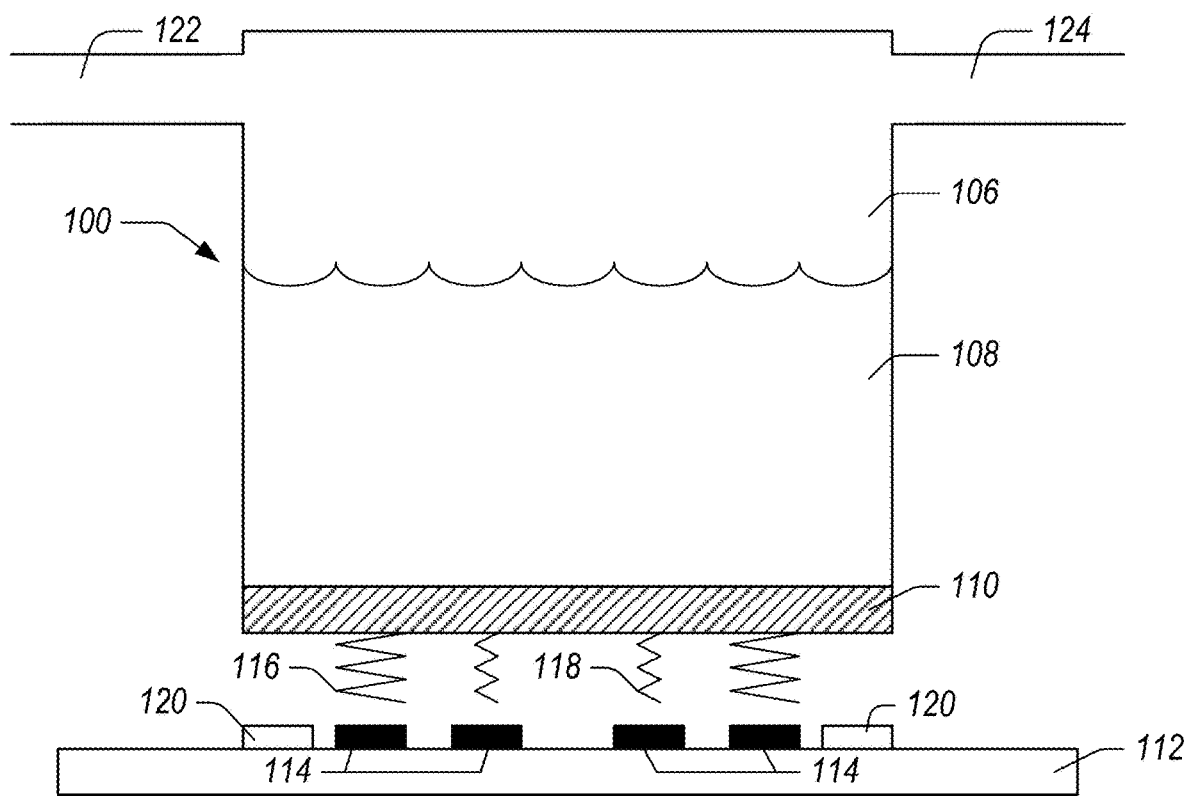
FIG. 3 is a depiction of a humidification system wherein conductive sensing elements have been placed on a surface of the humidification chamber.

FIG. 3 illustrates a configuration of a humidification system 100 that seeks to solve at least one of the above problems. In this configuration, the system 100 comprises two or more conductive spill elements 120 on the base unit 112. In some configurations, the spill elements 120 may be described as metallic substantially ellipse-shaped pads. In some configurations the spill elements 120 may be etched or printed circuits on a substrate. The elements 120 may be used in, for example, an amperometric sensing method. In some such configurations a voltage may be applied to one of the spill elements 120 (e.g. the 'first' element 120), and the other spill element 120 (e.g. the 'second' element 120) may be connected to an input pin of a controller (for example, a microprocessor) (not shown). The voltage of the second element 120 may have a floating state if there is no connection between the spill elements 120. In some configurations, a resistor could be used to improve reliability of the system by steering the voltage of the second element 120 to a known default state if no connection has been made between the spill elements 120. When water passes over the elements 120, a conductive or resistive pathway between the elements 120 may be established through the water. In such a situation, the voltage applied to the first element 120 may be used to pull up the voltage of the second element 120. When this electrical connection between the elements 120 is realized, one or more of the elements 120 may send a signal to the controller that may trigger an event causing the power source (not shown) of the system 100 to stop delivering current to the heating element 110 until the elements 120 fail to establish such an electrical connection (e.g. when the elements are sufficiently dry).

Figure 4:
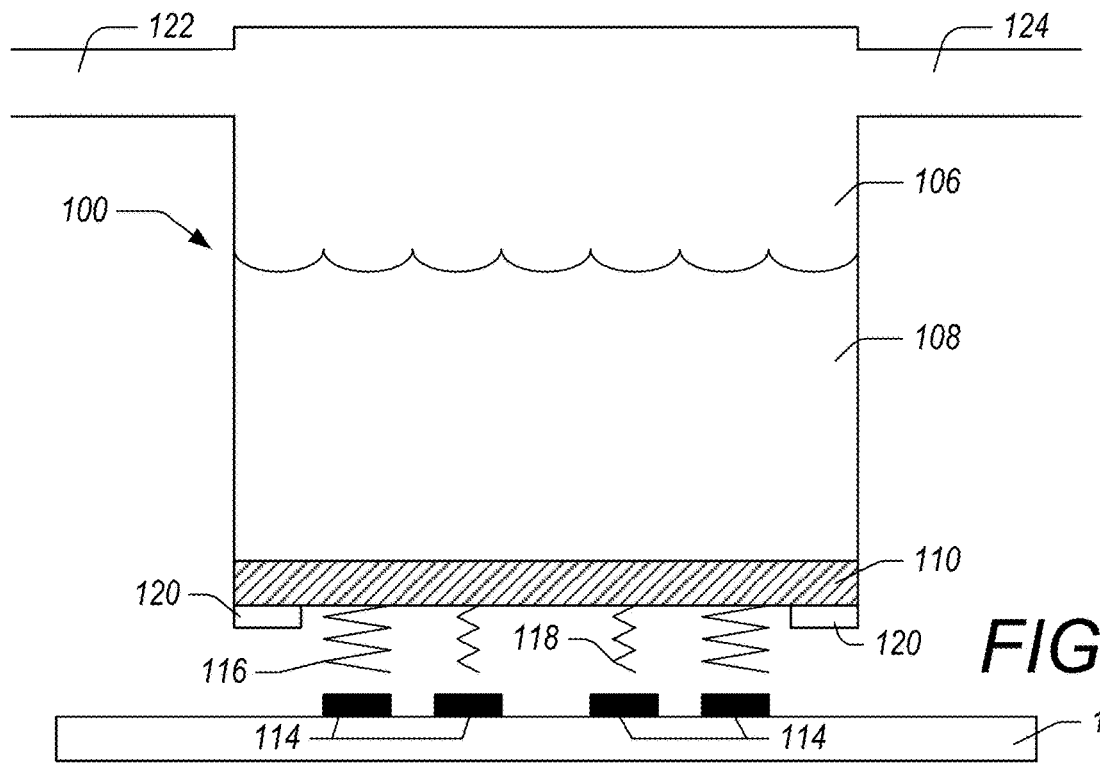
FIG. 4 is a depiction of a humidification system wherein conductive sensing elements have been placed on a surface of the water tub.

Advantageously, the system 100 may be protected from galvanic corrosion that may result from current running through spilt water. The conductive spill elements 120 may be placed in other locations in the system 100 where a water spill is expected to occur. In some configurations, and as illustrated in FIG. 4, the elements 120 may be placed on the bottom surface of the tub 106 and/or on the bottom surface of the heating element 110. In some configurations, the elements 120 may be placed on the external side walls of the tub 106 or the walls (not shown) of the base unit 112. In some configurations one or more of the elements 120 may be on the same side as the positive contact terminal of the heating element 110 (for example, the heater plate).

In some configurations, electrical energy in the form of a direct current (DC) may be applied to the elements 120 to check for an electrical connection between the spill elements 120. In some configurations, an alternating current (AC) may be applied to the elements 120 to check for an electrical connection between the spill elements 120.

In some configurations, the elements 120 may be conductive pads. In some configurations, the elements 120 may be terminals for connection to thermistors or other electronic systems. In some configurations, the elements 120 may be a combination of conductive pads and terminals.

Although the above paragraph describes one possible sensing mechanism, any means, structures or configurations by which excess water may be detected on the tub 106 and/or the base unit 112 may be used. In some configurations, the elements 120 may be capacitive sensing elements 120 that may be used to detect the presence of water. The elements 120 may be in close proximity with one another. Preferably, the elements 120 do not physically touch each other. Advantageously, the elements 120 may comprise a dielectric material covering the elements 120, which may isolate the elements 120 from the water while still permitting excess water sensing by the elements 120. Each element 120 may comprise fingers that spatially interlock (but preferably do not physically meet) with fingers of the other element 120. Capacitance between the pads may depend on the surroundings, and may be different in the presence of water. The capacitance in the presence of water could be considered a signal that water is present in the vicinity of the electrical connections, and this information could be sent to the controller to stop or otherwise alter the supply of power to the connections as described herein.

In some configurations, the sensing mechanism could occur passively or without the use of a controller (e.g. a microprocessor). As a voltage is applied to the first element 120, if water is present between the elements 120, a non-zero voltage will be present at the second element 120. A comparator may be used to compare the voltage across the second element 120 to a reference voltage. If the circuit used is an open-loop circuit, an operational amplifier or OP-AMP may be used as a comparator, however many electrical components may be used as comparators. A signal may be generated by the comparator and may be sent downstream to a gate. In some configurations, the gate may be a field-effect transistor or FET, for example a metal-oxide-semiconductor FET or MOSFET. If the signal from the comparator indicates that the voltage across the second element 120 exceeds the reference voltage (e.g. if water is present between the elements 120), the gate may be used to switch off power to the elements 120.

Figure 5:
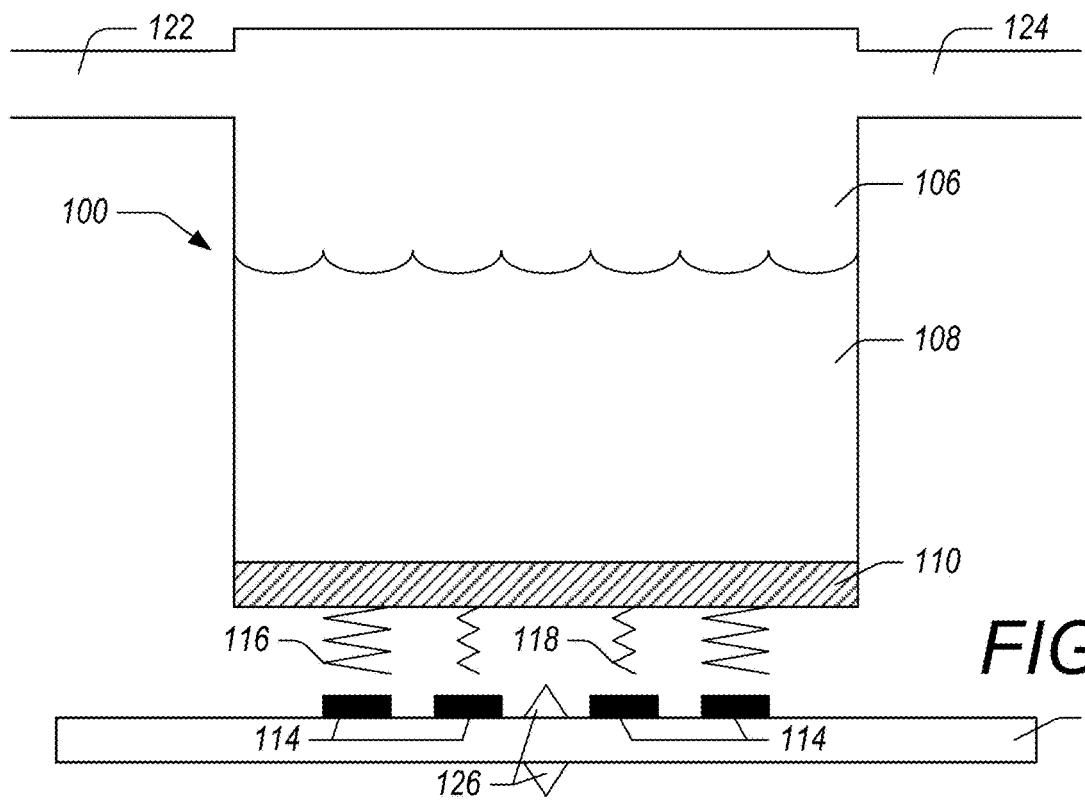
FIG. 5 is an exemplary sealing structure for use with a humidification chamber wherein conductive sensing elements have been placed on the surface of the sealing structure.

In some configurations, and as illustrated in FIG. 5, a pair of thermistors 126 may be placed on opposing sides of the base unit 112. In some such configurations, the elements 120 need not be present. The thermistors 126 may be exposed to a heat source, for example the heating element 110, or may be heated by the current running through the thermistors 126. If water is spilled over the thermistor on the side of the base unit 112 closest to the tub 106, a current may be applied to the thermistors and a voltage may be read across the terminals of the thermistors in order to estimate resistance and/or temperature. Upon contact with water, a resistance and/or temperature differential may be created between the thermistors 126 that signals the presence of water in the space between the tub 106 and the base unit 112. In such a scenario, a signal may be sent to a controller to cut off or otherwise alter power to the heating element 110 as described herein. In some configurations, a single thermistor 126 may be used as a water sensor. In some such configurations, the rate of change of temperature of the thermistor 126 may be calculated at two different times, or the rate of change of temperature may be compared to a predetermined threshold value that may be determined by a calibration step or may be preset. If the rate of change corresponds to a value that would be expected if the thermistor 126 was moistened with water, a signal may be sent to a controller to cut off or otherwise alter power to the heating element 110 as described herein. In some configurations, if a pair of thermistors 126 are used, the thermistors 126 may both be placed in the same thermal environment (e.g in the region of the water spill) if one of the pair of thermistors 126 can be protected from moisture.

Figure 6:
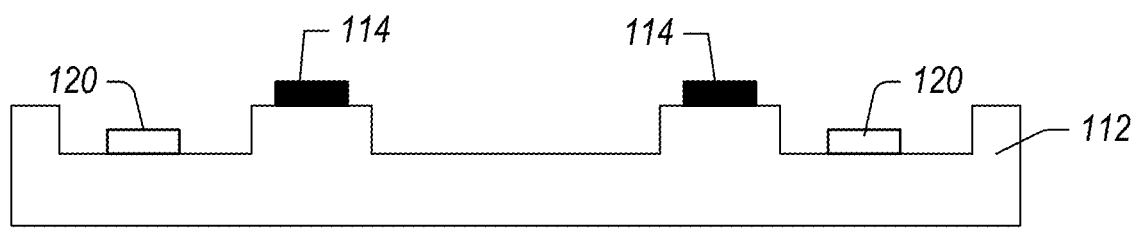
FIG. 6 illustrates an example surface of a base unit configured to channel water into a recessed portion to detect the presence of water so that the water is separated from electrical terminals.

FIG. 6 illustrates an example surface of a base unit 112 configured to channel water into a recessed portion of the base unit 112 to detect the presence of water with sensors 120 so that the water is separated from electrical terminals 114. The base unit 112 can be configured such that spilled water is encouraged (e.g., through gravity) to collect in a region separate from the electrical terminals 114 to resist or prevent water-related damage or other undesirable effects. In the illustrated example, the base unit is configured to have recessed portions. The recessed portions can be annular, compartmentalized, or any other suitable configuration. The terminals 114 can be configured to be physically raised from a surface of the base unit 112 so that spilled water does not pool or collect on or near the terminals 114. The recessed portion can be coupled to a draining portion to assist in the removal of water from the base unit 112.

The base unit 112 can have one or more water sensors 120 in the recessed portions of the base unit 112. This configuration may advantageously detect the presence of water on the base unit 112 before water-related problems occur in relation to the terminals 114. The sensors 120 can be configured to be physically lower than the electrical terminals 114 so that water is detected prior to the water level reaching the terminals 114.

Figure 7:
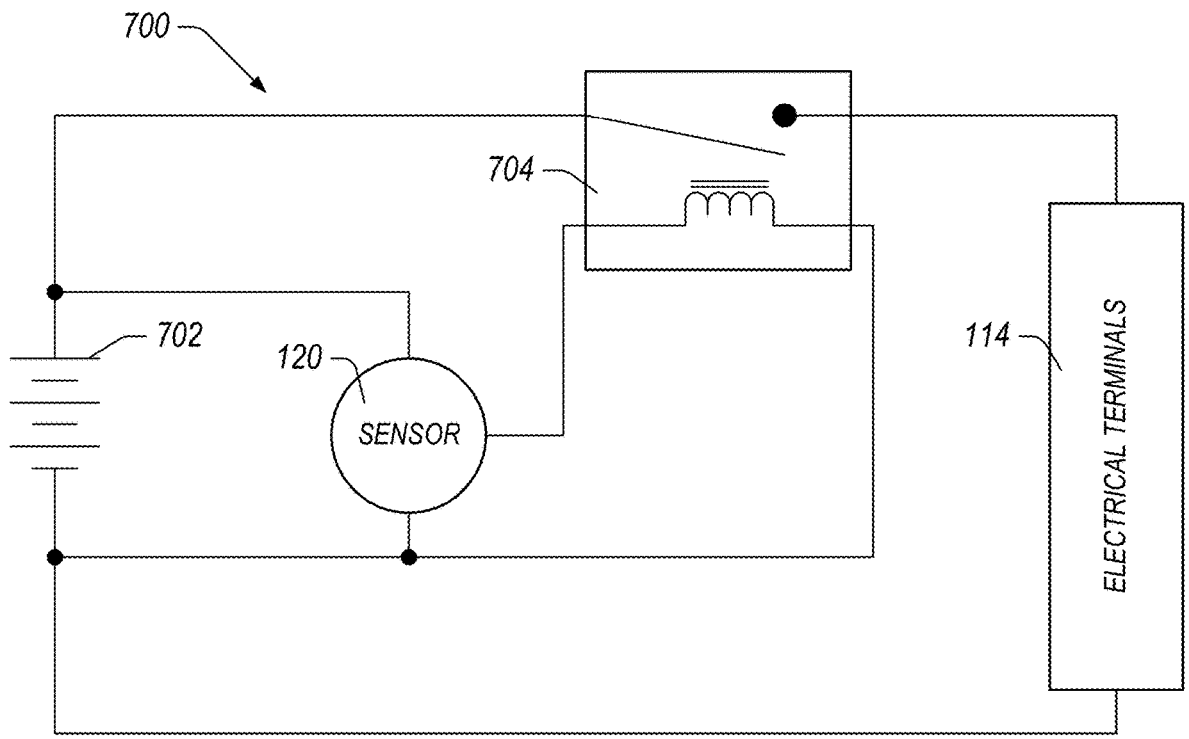
FIG. 7 illustrates an example circuit for controlling power to electrical contacts based at least in part on the output of a water sensor.

FIG. 7 illustrates an example circuit 700 for controlling power to electrical contacts 114 based at least in part on the output of a water sensor 120. The circuit 700 can include a power source 702 (e.g., a battery) configured to supply power to the terminals 114 through a switch or relay 704. The sensor 120 can be electrically coupled to the relay 704 to control whether the switch in the relay 704 is open or closed. In this way, the circuit 700 can control power to the terminals 114 by sending a signal to open the switch in the relay 704 when the sensor detects the presence of water. In the absence of water, the sensor 120 can send a signal to the relay 704 so that the switch in the relay 704 is closed, allowing power to flow from the power source 702 to the terminals. The circuit 700 is an example of a hardware control of power to the terminals 114. Other variations are possible, such as circuits that include transistors or other electrical components configured to regulate the flow of electrical power to the terminals 114 based at least in part on signals from the sensor 120. Circuits can also include additional elements configured to allow other inputs to the relay 704 or other similar power-controlling element so that whether power is provided to the terminals is based on a number of factors. The sensor 120 can comprise one or more sensors.

Figure 8:
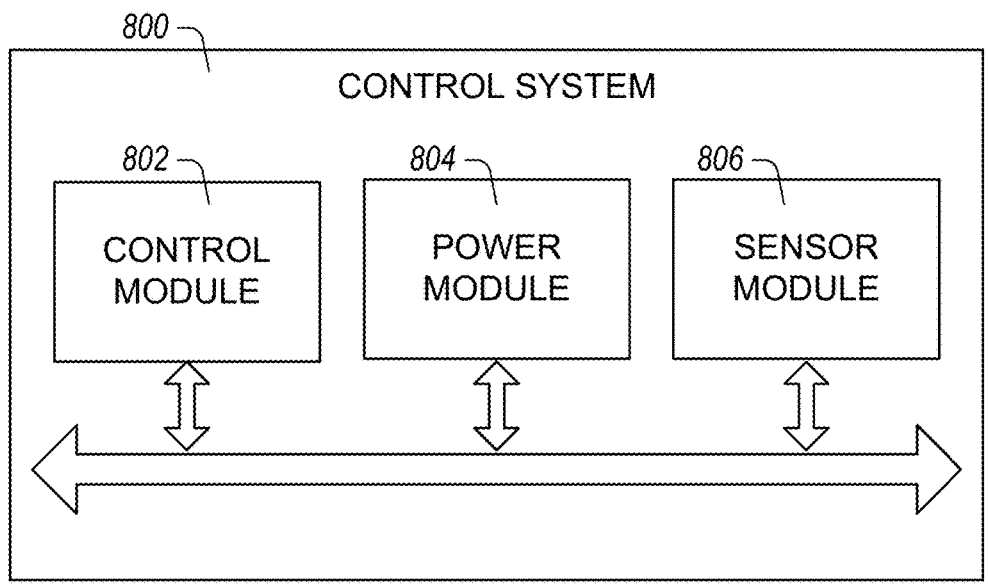
FIG. 8 illustrates a block diagram of an example control system for a humidification chamber.

FIG. 8 illustrates a block diagram of an example control system 800 for a humidification chamber 100. The control system 800 can include a control module 802, a power module 804, and a sensor module 806. The control module 802 can communicate with the power module 804 and the sensor module 806 to regulate power delivered to a heating element and/or electrical terminals. In general, when the sensor module 806 detects fluid on the base unit, the control module 802 instructs the power module 804 to restrict and/or substantially terminate the flow of electrical power.

In certain implementations, the control module 802 includes one or more processors that communicate with the sensor module 806 and/or the power module 804. For example, such a processor may be mounted on a printed circuit board within the control module 802. The control module 802 can be configured to receive a signal from the sensor module 806 when the sensor module 806 detects fluid (e.g., water). The processor can then output a control signal to the power module 804 to restrict electrical power to terminals (e.g., terminals 114).

The control module 802 can be configured to communicate with the sensor module 806 that is coupled to one or more sensors (e.g., sensor(s) 120). In certain implementations, when the sensor module 806 detects fluid, such as by coming in contact with water, a conductive path is effectively created between sensor contacts (e.g., where the sensor 120 comprises conductive elements situated close together). This can cause the sensor module 806 to provide a signal to the control module 802 to shut off power to electrical terminals. The control module 802 can then signal the power module 804 to terminate power delivery. In some embodiments, the control module 802 can also cause an alert or alarm (e.g., audio or visual indication) of when the sensor module 806 detects fluid. For example, the control module 802 can display a message (e.g., on a display) when liquid is detected by the sensor module 806. The control module 802 can be electrically coupled to the power module 804 such that data and/or control communication may take place therebetween.

The control module 802 is coupled to the sensor module 806 and the power module 804, and is configured to output a first control signal to cause the power module 806 to disconnect or terminate the delivery of electrical power when the sensor module 806 is providing a first voltage level corresponding to water detection. The control module 802 is further configured to output a second control signal to cause the power module 804 to provide electrical power when the sensor module 806 provides a second voltage level corresponding to no detected water.

In some embodiments, the sensor 120 is configured to form a closed circuit when a fluid, such as a conductive liquid, contacts the surface of the sensor 120. For example, the sensor 120 may comprise a strip sensor that is placed on a surface of the base unit 112. Contact of the sensor 120 with water acts to close a circuit. When the circuit is closed, the control module 802 signals the power module 804 to stop the flow of power. In one arrangement, the sensor 120 can be a tin-lead or zinc-coated copper sensor or other type of sensor.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to." The disclosed embodiments may also be said broadly to consist in the parts, elements and features referred to or indicated in the specification of the application, individually or collectively, in any or all combinations of two or more of said parts, elements or features.

Certain features, aspects and advantages of some configurations of the present disclosure have been described with reference to use by a patient or user. However, certain features, aspects and advantages of the use of the humidification system as described may be advantageously practiced by other people on behalf of the patient, including medical professionals, medical device dealers, or medical device providers. Certain features, aspects and advantages of the methods and apparatus of the present disclosure may be equally applied to usage by other people.

Certain features, aspects and advantages of some configurations of the present disclosure have been described with reference to a respiratory therapy humidifier. However, certain features, aspects and advantages of the humidification system as described above may be advantageously used with non-therapeutic humidification devices, such as room humidifiers, or other systems in which electrical connections may be exposed to water or other liquids, such as coffee makers or water heating devices. Certain features, aspects and advantages of the methods and apparatus of the present disclosure may be equally applied to such devices.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A humidification system for use with a respiratory therapy device, the humidification system comprising:
   a tub configured to hold a humidification agent, the tub comprising an inlet and an outlet configured to allow gas to move to and from the tub;
   a heating element configured to be in thermal communication with the tub when the tub is removably positioned on the heating element;
   a circuit configured to control power to the heating element, the circuit comprising
      a power source configured to provide power to the heating element;
      one or more electrical contacts in contact with the heating element, the one or more electrical contacts coupled to the power source to deliver power from the power source to the heating element;
      a switch or relay connected in series with the one or more electrical contacts, the switch or relay located between the one or more electrical contacts and the power source, wherein the switch or relay is moveable between an open position and a closed position, and wherein:
         when the switch or relay is in the open position, the one or more electrical contacts are disconnected from the power source, and
         when the switch or relay is in a closed position, the one or more electrical contacts are connected to the power source; and
      a sensor electrically coupled to the switch or relay and located away from an inner surface of the tub, wherein the sensor is configured to detect presence of the humidification agent at a location of the system outside the tub, wherein the circuit is configured to send a first signal to open the switch or relay so as to break the circuit between the power source and the one or more electrical contacts when the sensor detects the presence of the humidification agent, and the circuit is configured to send a second signal to close the switch or relay so as to complete the circuit between the power source and the one or more electrical contacts when the sensor detects no presence of the humidification agent.

2. The humidification system of claim 1, wherein the sensor comprises conductive elements situated close together so as to detect the presence of the humidification agent by forming a closed circuit when the humidification agent contacts a surface of the sensor.

3. The humidification system of claim 1, wherein the sensor comprises a strip sensor placed on a surface of a base unit of the humidification system, wherein the base unit is configured to removably receive the tub.

4. The humidification system of claim 1, wherein the sensor comprises a tin-lead or zinc-coated copper sensor.

5. The humidification system of claim 1, wherein the switch or relay comprises a solenoid.

6. The humidification system of claim 1, wherein the circuit further comprises one or more electrical components configured to regulate the flow of power to the one or more electrical contacts.

7. The humidification system of claim 6, wherein the one or more electrical components comprise a transistor.

8. The humidification system of claim 1, wherein the sensor is connected in parallel with the power source.

9. The humidification system of claim 1, further comprising a base unit, wherein a push-down or drop-in electrical connection is formed between the heating element and the one or more electrical contacts when the tub is engaged with the base unit.

10. The humidification system of claim 1, wherein the circuit further comprises a controller, wherein the controller is configured to send the first or second signal to open or close the switch or relay.

11. The humidification system of claim 1, wherein the heating element is not integrated into the tub.

12. A humidification system for use with a respiratory therapy device, the humidification system comprising:
a tub configured to hold a humidification agent, the tub comprising an inlet and an outlet configured to allow gas to move to and from the tub;
a heating element configured to be in thermal communication with the tub when the tub is removably positioned on the heating element;
a control system configured to control power to the heating element in the presence of the humidification agent detected on or about the heating element, the control system comprising:
a control module including one or more processors in electrical communication with a sensor module and a power module, the control module configured to receive signals from the sensor module and process the signals to determine the presence of the humidification agent detected by the sensor module, the control module further configured to control the power module by outputting a first control signal to restrict or substantially terminate power to the heating element in response to the humidification agent being detected by the sensor module and outputting a second control signal to supply power to the heating element in response to no humidification agent being detected by the sensor module; and
a hardware circuit including a switch or relay and a sensor, wherein the sensor is configured to detect the presence of the humidification agent and provide a switch or relay control signal to open the switch or relay in response to detection of the presence of the humidification agent by the sensor and close the switch or relay in response to no detection of the presence of the humidification agent by the sensor, wherein the sensor module is coupled to the sensor.

13. The humidification system of claim 12, wherein the control module is further configured to output an alert or alarm in response to the sensor module detecting the humidification agent.

14. The humidification system of claim 13, wherein the control module is further configured to output a message to be displayed on a display device in response to the sensor module detecting the humidification agent.

15. The humidification system of claim 12, wherein the control module is configured to output the first control signal in response to the sensor module providing a first voltage level corresponding to the humidification agent being detect and the control module is configured to output the second control signal in response to the sensor module providing a second voltage level corresponding to no humidification agent being detected.

16. The humidification system of claim 12, wherein the sensor comprises conductive elements situated close together so as to detect the presence of the humidification agent by forming a closed circuit when the humidification agent contacts a surface of the sensor.

17. The humidification system of claim 12, wherein the sensor comprises a strip sensor placed on a surface of a base unit of the humidification system, wherein the base unit is configured to removably receive the tub.

18. The humidification system of claim 12, wherein the sensor comprises a tin-lead or zinc-coated copper sensor.

19. The humidification system of claim 12, wherein the hardware circuit further comprises a power source configured to provide power to the heating element.

20. The humidification system of claim 12, wherein the hardware circuit further comprises one or more electrical contacts in contact with the heating element, the one or more electrical contacts coupled to the power source to deliver power from the power source to the heating element.

\* \* \* \* \*